US009845674B2

(12) United States Patent
Hurst et al.

(10) Patent No.: US 9,845,674 B2
(45) Date of Patent: Dec. 19, 2017

(54) CONCENTRATION DETERMINING METHOD AND SYSTEM

(71) Applicant: BP EXPLORATION OPERATING COMPANY LIMITED, Middlesex (GB)

(72) Inventors: Shuan Raymond Hurst, Hertfordshire (GB); Roderic Lewis Jones, Cambridgeshire (GB)

(73) Assignee: BP EXPLORATION OPERATING COMPANY LIMITED, Middlesex (GB)

( * ) Notice: Subject to any disclaimer, the term of this patent is extended or adjusted under 35 U.S.C. 154(b) by 27 days.

(21) Appl. No.: 14/908,175

(22) PCT Filed: Jul. 23, 2014

(86) PCT No.: PCT/EP2014/065857
§ 371 (c)(1),
(2) Date: Jan. 28, 2016

(87) PCT Pub. No.: WO2015/014694
PCT Pub. Date: Feb. 5, 2015

(65) Prior Publication Data
US 2016/0168986 A1    Jun. 16, 2016

(30) Foreign Application Priority Data

Jul. 31, 2013    (EP) .................................... 13178796

(51) Int. Cl.
*G01N 21/00* (2006.01)
*E21B 49/08* (2006.01)
(Continued)

(52) U.S. Cl.
CPC .............. *E21B 49/08* (2013.01); *C09K 8/528* (2013.01); *E21B 37/06* (2013.01); *G01N 21/33* (2013.01);
(Continued)

(58) Field of Classification Search
CPC ........ G01N 21/33; G01N 30/74; C09K 8/528; E21B 2049/085; E21B 37/06; E21B 49/08
(Continued)

(56) References Cited

U.S. PATENT DOCUMENTS 7,943,058 B2    5/2011  Hills et al.
2007/0267193 A1  11/2007  Hills et al.

FOREIGN PATENT DOCUMENTS

WO    WO 2012/018683 A1    2/2012
WO    WO 2012/098186 A1    7/2012

*Primary Examiner* — Tri T Ton
(74) *Attorney, Agent, or Firm* — Conley Rose, P.C.

(57) ABSTRACT

A computer-implemented method and corresponding system for determining the concentration of one or more scale inhibiting polymers in a fluid received from one or more porous and permeable hydrocarbon-bearing rock formations is provided. Each polymer comprises a different chemical marker and the fluid comprises a plurality of commingled said scale inhibiting polymers. The method comprises receiving first input data representing a measured absorption spectrum, within a predetermined wavelength range, of the commingled scale inhibiting polymers, wherein the measured absorption spectrum is measured using a detector after chromatographic separation of the fluid; receiving second input data representing reference absorption spectra, the reference absorption spectra comprising: a) an absorption spectrum, over the predetermined wavelength range, of each of the scale inhibiting polymers; and b) baseline reference absorption spectra of other chemicals having absorbance values within the predetermined wavelength range that are
(Continued)

expected to be present in the fluid; inputting the first and second input data into a computer program; and operating the computer program. The computer program is operated to, at each of a plurality of discrete time steps over an elution time from the separation, determine a factor for each reference absorption spectrum that results in a modelled spectrum comprising a best-fit linear combination of the second input data to the first input data. For each scale inhibiting polymer, the computer program also operates to use the factors corresponding to the absorption spectrum of said scale inhibiting polymer that have been determined for a predetermined number of said discrete time steps to determine an indication of the concentration of the scale inhibiting polymer.

19 Claims, 10 Drawing Sheets

(51) Int. Cl.
*G01N 21/33* (2006.01)
*E21B 37/06* (2006.01)
*C09K 8/528* (2006.01)
*G01N 30/74* (2006.01)

(52) U.S. Cl.
CPC ........ *G01N 30/74* (2013.01); *E21B 2049/085* (2013.01)

(58) Field of Classification Search
USPC .................................................. 356/432–448
See application file for complete search history.

CONCENTRATION DETERMINING METHOD AND SYSTEM

This application is the U.S. national phase of International Application No. PCT/EP2014/065857 filed Jul. 23, 2014 which designated the U.S. and claims priority to European Patent Application No. 13178796.2 filed Jul. 31, 2013, the entire contents of each of which are hereby incorporated by reference.

TECHNICAL FIELD

The present invention relates to a computer-implemented method and a system for determining the concentration of one or more scale inhibiting polymers, each polymer comprising a different chemical marker, in a fluid comprising a plurality of commingled said scale inhibiting polymers.

BACKGROUND

The formation of scale (which can be defined as the solid precipitates that form in aqueous systems when, due to changes in the physical or chemical environment of the system, the solubility limits of certain compounds are exceeded) presents a problem in many industrial operations involving aqueous fluids, for instance oil and gas industry applications, mineral ore extraction, paper manufacture and geothermal power generation. In the oil and gas industry in particular, scale deposition on equipment surfaces may cause obstructions or blockages, leading to costly interruptions in production and safety risks from unforeseen pressure build-up. In oil and gas wells and associated equipment such as wellheads, flowlines or other processing or transportation equipment, the formation of scale is largely due to destabilisation through pressure and temperature changes in formation water and the mixing of incompatible aqueous fluids. For instance, when seawater is used as an injection fluid to drive oil through a subterranean formation towards a production well, differences in the ionic content of the injected seawater and the ionic content of the connate water of the formation can lead to the precipitation of inorganic salts. In the absence of suitable treatment, the precipitated salts form a scale which obstructs the flow of oil towards production wells and accumulates on production equipment, leading ultimately to the blockage of the production well. Similarly, precipitated salts can form scale build up on equipment associated with hydrocarbon production, processing and transportation.

Scale inhibitors are widely used in the oil and gas industry. Problems of scaling on equipment surfaces may be addressed by the continuous injection of scale inhibitors into the equipment. To prevent the formation of scale within oil/gas-bearing formations, two techniques are generally used. In one approach, a scale inhibitor may be included in a fluid (typically an aqueous fluid) to be injected into the formation via one or more injection wells, e.g. to flush oil towards a production well (water flooding treatment). In another approach, known as a "squeeze treatment", a fluid containing a scale inhibitor (again typically an aqueous fluid) can be introduced into a production well (after production is stopped) so as to "squeeze" the scale inhibitor into the rock formation surrounding the production well. In this way, scale inhibitors are delivered to the formation rock so as to prevent the formation of scale deposits both in the formation itself (pore blockage) and subsequently in downstream production apparatus.

Scale formation can be controlled only if a scale inhibitor is provided in sufficient quantity. In the case of "squeeze treatment", the concentration of scale inhibitor will reduce over time until a repeat treatment of the scale inhibitor is required (a "re-squeeze" treatment). It would therefore be very useful to be able to analyse the fluid produced from a production well in order to ensure that the concentration of scale inhibitor is always maintained at a level at which scale formation is sufficiently inhibited. By analysing the level of scale inhibitor in produced fluids, the depletion of scale inhibitor concentration can be monitored, and thus the need for repeat treatments of scale inhibitors can be determined. It is desirable that the level of scale inhibitors can be determined accurately, so as to avoid the need to carry out re-squeeze treatments more often than is strictly necessary, as a precautionary measure against the risk of scale deposit and consequent loss of production. Providing more scale inhibitor than is required is undesirable both due to the cost of excess scale inhibitor and due to the interruption of production that is required each time a re-squeeze treatment is carried out.

In modern oil production fields, it is increasingly common for produced fluids from a number of production wells to be combined and transported to a production facility in a single pipeline. In particular, in subsea production, it is common for the fluids from a number of production wells to be combined on the seabed, for example in a manifold, and piped to the nearest production platform, which may be many miles away. There is therefore a need for a means of analysing the level of scale inhibitor in the produced fluids from each individual well in order to ensure that individual wells do not lose production due to scale build-up. Currently, this analysis can be done in two different ways. Firstly, by turning off the flows from all but one well, the level of scale inhibitor in the one remaining well may be determined. However, this approach is not commercially viable due to the significant loss in production entailed as each individual well is tested. Furthermore, hydraulic limitations may hinder production from a single well back to a test facility. The second approach involves using different scale inhibitors in each production well, such that the level of each may be determined by analysis of the commingled flow. However, not all scale inhibitors are equally effective and, since the number of scale inhibitors required is the same as the number of wells, a situation is rapidly reached where less than optimal scale inhibitors must be used in some wells simply to ensure that each well has a different scale inhibitor. This leads to poorer scale inhibition in certain wells and therefore a requirement for more interventions in those wells than might otherwise be the case could more effective scale inhibitors be used.

It has been proposed to prepare scale inhibiting polymers which differ from one another in that they include a small number of chemical markers in the form of tagging moieties, the tagging moieties of each polymer being different from the tagging moiety of the other polymers. It is expected that, because the tagging moiety is included in the polymer in relatively small numbers, the scale inhibiting properties of the polymer will be largely unchanged from a polymer with no such tagging moieties. In this way, more than one well can be treated with an effective scale inhibitor whilst still permitting identification of the scale inhibitor in the commingled produced flow. However, the oil and gas industry has so far failed to produce a robust detection technique that accurately detects the presence and concentration of scale inhibitors in produced fluid, particularly where multiple tagged scale inhibitors are commingled and a single, optimal scale inhibitor is ideally required to treat all associated rock formations as effectively as possible.

SUMMARY

According to a first aspect of the present invention, there is provided a computer-implemented method of determining the concentration of one or more scale inhibiting polymers, each scale inhibiting polymer comprising a different chemical marker, in a fluid received from one or more porous and permeable hydrocarbon-bearing rock formations, the fluid comprising a plurality of commingled said scale inhibiting polymers, the method comprising:

receiving first input data representing a measured absorption spectrum, within a predetermined wavelength range, of the commingled scale inhibiting polymers, wherein the measured absorption spectrum is measured using a detector after chromatographic separation of the fluid;

receiving second input data representing reference absorption spectra, the reference absorption spectra comprising:
a) an absorption spectrum, over the predetermined wavelength range, of each of the scale inhibiting polymers; and
b) baseline reference absorption spectra of other chemicals having absorbance values within the predetermined wavelength range that are expected to be present in the fluid;

inputting the first and second input data into a computer program; and operating the computer program to perform the steps of:
at each of a plurality of discrete time steps over an elution time for the separation, determining a factor for each reference absorption spectrum that results in a modelled spectrum comprising a best-fit linear combination of the second input data to the first input data; and
for each scale inhibiting polymer:
using the factors corresponding to the absorption spectrum of said scale inhibiting polymer that have been determined for a predetermined number of said discrete time steps to determine an indication of the concentration of the scale inhibiting polymer.

The present invention further provides a system arranged to determine the concentration of one or more scale inhibiting polymers, each scale inhibiting polymer comprising a different chemical marker, in a fluid received from one or more porous and permeable hydrocarbon-bearing rock formations, the fluid comprising a plurality of commingled said scale inhibiting polymers, the system comprising:

data receiving means arranged to receive:
first input data representing a measured absorption spectrum, within a predetermined wavelength range, of the commingled scale inhibiting polymers, wherein the measured absorption spectrum is measured using a detector after chromatographic separation of the fluid; and
second input data representing reference absorption spectra, the reference absorption spectra comprising:
a) an absorption spectrum, over the predetermined wavelength range, of each of the scale inhibiting polymers; and
b) baseline reference absorption spectra of other chemicals having absorbance values within the predetermined wavelength range that are expected to be present in the fluid;

concentration determining means configured to:
at each of a plurality of discrete time steps over an elution time for the separation, determine a factor for each reference absorption spectrum that results in a modelled spectrum comprising a best-fit linear combination of the second input data to the first input data; and
for each scale inhibiting polymer:
use the factors corresponding to the absorption spectrum of said scale inhibiting polymer that have been determined for a predetermined number of said discrete time steps to determine an indication of the concentration of the scale inhibiting polymer.

In a situation where produced fluid from multiple rock formations and associated production wells is combined in a "commingled" flow, a sample of the commingled fluid can be taken at a convenient location and analysed in accordance with the computer-implemented method and system of the present invention to detect and determine the concentration of one or more scale inhibiting polymers, each polymer comprising a different chemical marker. The polymer backbone may be the same or different. The invention allows for the same scale inhibitor to be used in the rock formation(s) of multiple hydrocarbon-bearing reservoirs and for produced fluid to be recovered via an efficient pipeline system, whilst allowing robust, accurate and sensitive monitoring of individual concentrations of scale inhibitors flowing from each production well.

The baseline reference absorption spectra comprise at least an absorption spectrum of each scale inhibiting polymer in the absence of its chemical marker, an absorption spectrum of produced fluid produced from the one or more rock formations, and an absorption spectrum of pure water comprising other chemicals having absorbance values within the predetermined wavelength range that are expected to be present in the fluid. Such other chemicals can be contaminants present in the laboratory where the method is being conducted.

In an embodiment, the computer program is operated to use the factors corresponding to the absorption spectrum of said scale inhibiting polymer that have been determined for a predetermined number of said discrete time steps by summing said factors.

Further features and advantages of the invention will become apparent from the following description of preferred embodiments of the invention, given by way of example only, which is made with reference to the accompanying drawings.

DETAILED DESCRIPTION

Figure 1:
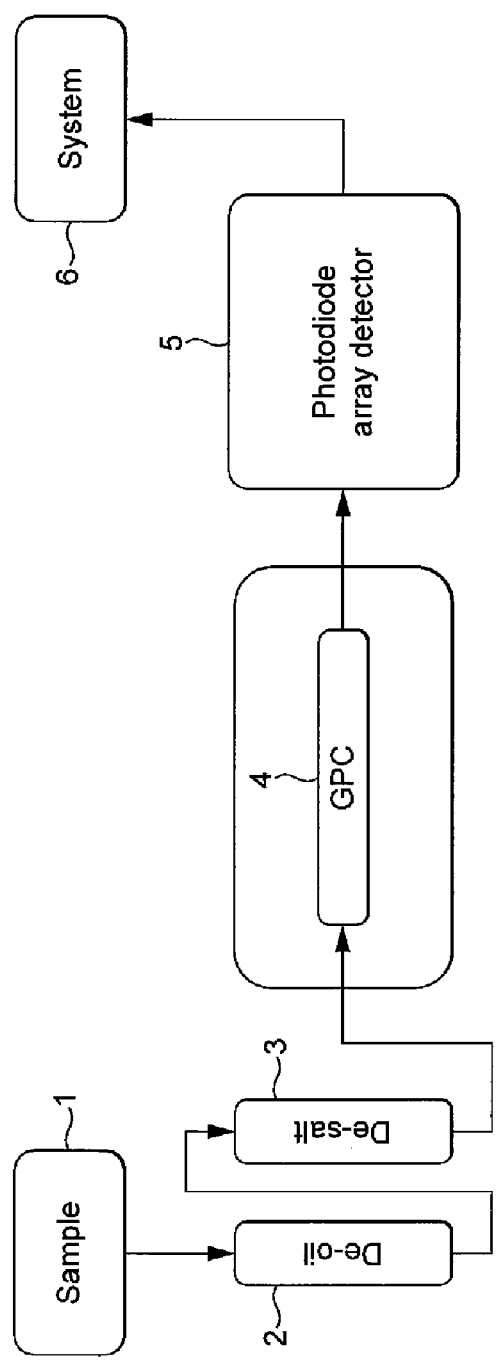
FIG. 1 shows an apparatus arranged to separate and detect the absorption spectra of different components of a fluid sample.

FIG. 1 shows an apparatus arranged to separate, and detect the absorption spectra of, different components of a fluid sample 1 such as an oil field brine sample that contains multiple commingled polymeric scale inhibitors having a common polymer "backbone" and different chemical markers or "tags". The apparatus is used to determine absorption spectra corresponding to chemically-tagged polymeric scale inhibitors (referred to herein as "tagged inhibitors") across a predetermined wavelength range. Tags that absorb in the ultraviolet-visible range, i.e. up to 700 nm, may be employed. In one example, the tags are monomers identified as absorbing in the UV region of the electromagnetic spectrum, and hence the measured absorption spectra are UV spectra across the wavelength range of 190 nm to 300 nm. It is to be understood that monomers identified as absorbing over other wavelength ranges could be used, in which case the absorption spectra would be measured across the appropriate wavelength range. In order to collect the UV spectra corresponding to the tagged inhibitors only it is necessary to separate the tagged inhibitors from all other UV absorbing species present in the oil field brine sample. Referring to FIG. 1, the fluid sample 1 is passed through a de-oiling device 2 comprising, for example, C18 solid phase extraction (SPE) cartridges, to remove oil present in the fluid sample 1. The fluid sample 1 is then passed through a de-salting device 3, for example three de-salting cartridges, to remove any residual salt that may affect the UV response of the tagged inhibitors (e.g. PD-10 Desalting Columns supplied by GE Healthcare, which contain Sephadex G-25 Medium and which allows rapid group separation of high molecular weight substances from low molecular weight substances). Gel permeation chromatography (GPC) is then performed by passing the fluid sample 1 through a GPC column 4 in order to separate the tagged inhibitors from other water soluble oil field production chemicals of different molecular weights and any residual salt. The mobile phase used in the GPC process is chosen to balance column reliability over time (which is less reliable at lower concentrations) with signal strength (which decreases at higher concentrations). In an example, the mobile phase used is 0.001 M sodium perchlorate in high performance liquid chromatography (HPLC) water, i.e. pure or de-ionised water. The stationary phase of the GPC column 4 may be, for example, PL aquagel-OH or PolarGel-L, supplied by Agilent Technologies.

A photodiode array (PDA) detector 5 is used in sequence with the GPC separation to perform ultraviolet-visible (UV-Nis) spectroscopy on the GPC eluate; in an example, the spectrum is measured every 0.1 seconds between wavelengths of 190 nm and 300 nm.

The spectra of the tagged inhibitors—separated from residual oil, salt and production chemicals, but still co-eluting with each other—are then de-convolved using a computer-implemented algorithm executed on a computer system 6 to enable the relative amounts (concentrations) of each tagged inhibitor present at that elution time to be determined. The algorithm is able to detect tagged inhibitors when they are present, while disregarding any additional UV/Vis absorptions from other sources.

Figure 2:
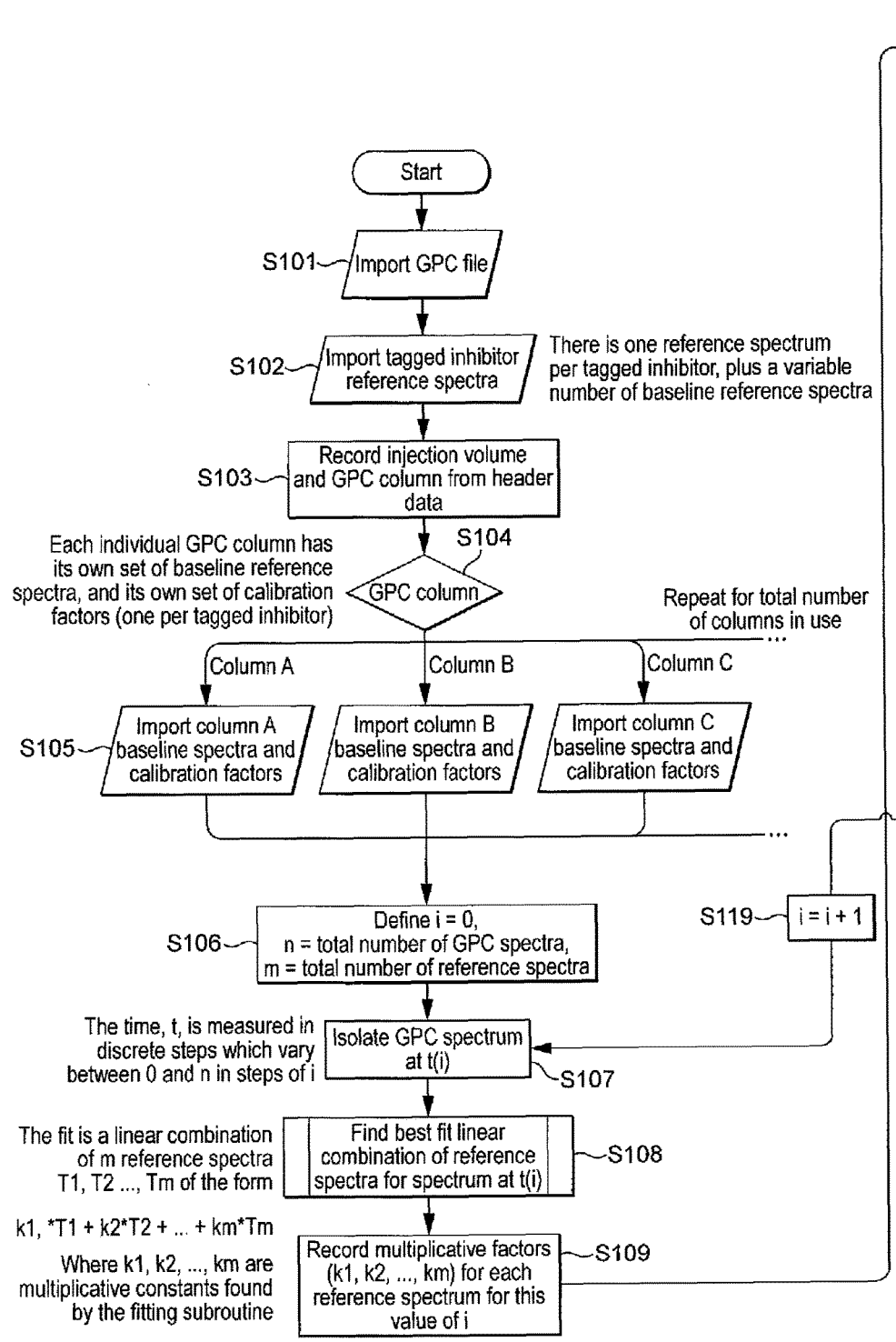
FIG. 2 shows the steps taken by a computer program configured to de-convolve the spectra detected by the apparatus of FIG. 1, according to an embodiment of the present invention.
Figure 2:
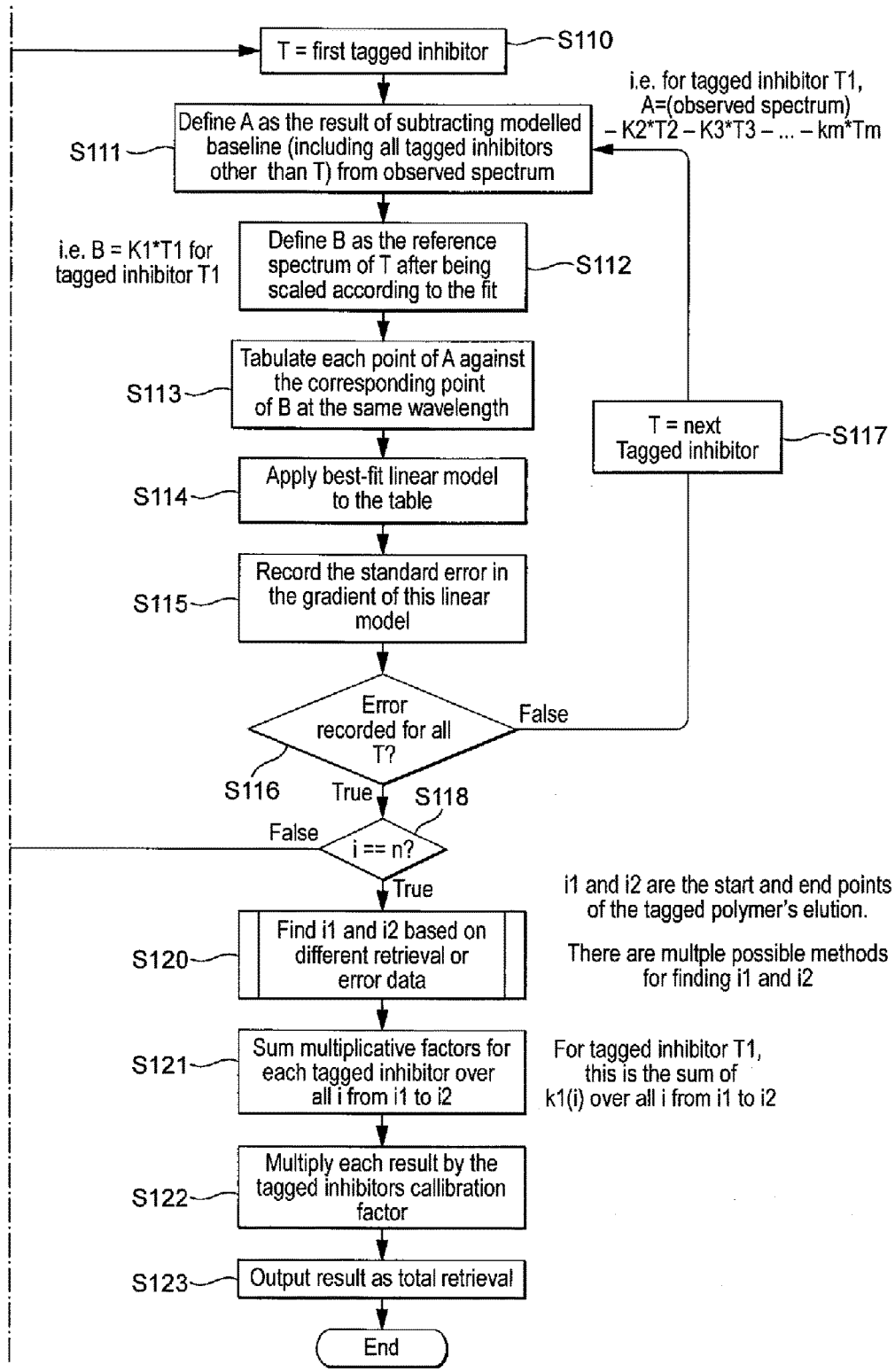

An example of a chemometric deconvolution algorithm according to the invention, which is configured to de-convolve the spectra detected by the apparatus of FIG. 1 so as to determine the concentrations of the tagged inhibitors in the fluid sample 1, is shown in FIG. 2. The algorithm is based around a best fit of a linear combination of a set of "curves" to each PDA spectrum in a GPC run. As explained further below, the curves are reference spectra which represent all known possible UV absorbances that are expected to be observed in the fluid sample 1. Once the best fit for a spectrum is found, the corresponding multiplicative factor for each curve is recorded. The detection process is performed independently for each individual spectrum; the relative amounts of each tagged inhibitor present are calculated for each UV/Vis spectrum sequentially. These relative amounts can then be plotted as a function of time. Integration under the resulting curves gives quantities which are proportional to the concentration of each tagged inhibitor.

Referring to FIG. 2, in step S101 data representing an experimental, measured absorption spectrum of the commingled tagged scale inhibitors present in the fluid sample 1 is received from the PDA detector 5 and input into the system 6. In the example described below with reference to FIGS. 3 to 12, the data input at step S101 represents a set of UV/Vis spectra between 190 and 300 nm at intervals of 1 nm, with a spectrum measured every 0.1 seconds for 30 minutes.

In steps S102 and S104, data representing the reference spectra is input into the system 6. In the example of FIGS. 3 to 12, all reference spectra are measured at intervals of 1 nm between 190 and 300 nm. The absorption spectra of FIGS. 3 to 10 show units of absorbance in mAU against wavelength in nanometers, nm.

Figure 3:
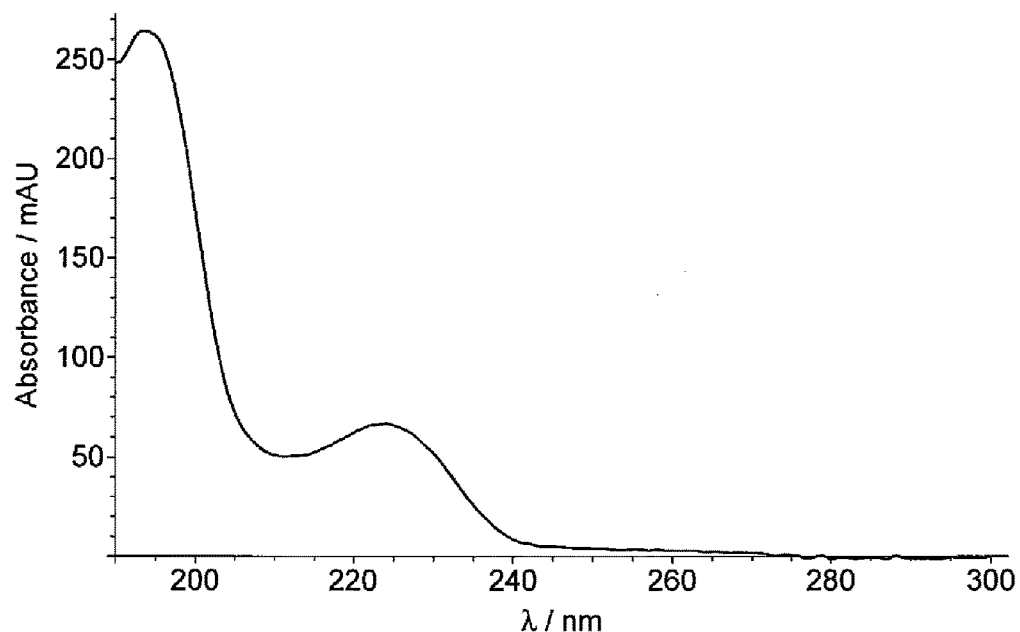
FIG. 3 shows a reference absorption spectrum of an example scale inhibiting polymer that is input into the computer program.

The reference spectra include at least one reference spectrum per tagged inhibitor, for example a "static" UV spectrum of each tagged inhibitor that is obtained by dissolving a sample of the tagged inhibitor in water and measuring the spectrum using a UV spectrophotometer. An example reference spectrum for one of the tagged inhibitors is shown in FIG. 3, with absorbance values in thousandths of an absorbance unit as defined by the PDA detector 5. Typical calibration factors for this tagged inhibitor are between approximately 1.3 and 1.6. For the specific conditions of the example shown in FIG. 3, the calibration factor is 1.37. This means that any indications of concentration output from the algorithm for this tagged inhibitor must be multiplied by 1.37 to obtain the absolute or true concentration. The calibration factor is derived by obtaining an output concentration $c_{out}$ from the algorithm for a single tagged inhibitor at a known concentration $c_{cal}$, and dividing $c_{cal}$ by $c_{out}$. This calibration process requires only one experiment at a known polymer concentration. The concentration chosen is typically 100 ppm, which is sufficiently high that PDA detector noise has a negligible effect on the spectrum across the entirety of the inhibitor's elution peak. Data representing the tagged inhibitor reference spectra of all tagged inhibitors present in the fluid sample 1 are input into the system 6 at step S102.

At step S103, a fluid sample 1 injection volume and identity of the GPC column (such that the algorithm can distinguish between experimental data relating to multiple different GPC columns) are input into the system 6.

The reference spectra also include a variable number of "baseline" reference spectra, of other chemicals having non-zero absorbance values within the predetermined wavelength range that are expected to be present in the fluid (and which do not correspond to UV tagged inhibitors) and which may co-elute. There are typically three classes of baseline reference spectra, differentiated by how they are derived: from the scale inhibiting polymer in the absence of any tag (the "untagged inhibitor"); from produced fluid produced from the one or more rock formations from which the fluid sample 1 is obtained (to account for absorbance values of other UV-active high molecular weight chemicals present in the produced water); and from water, such as pure/HPCL water, comprising other chemicals having absorbance values within the predetermined wavelength range that are expected to be present in the fluid—this typically involves measuring static UV spectra of pure (HPLC) water before and after exposure to laboratory air, to account for exposure of the fluid sample 1 to laboratory contaminants.

Figure 4:
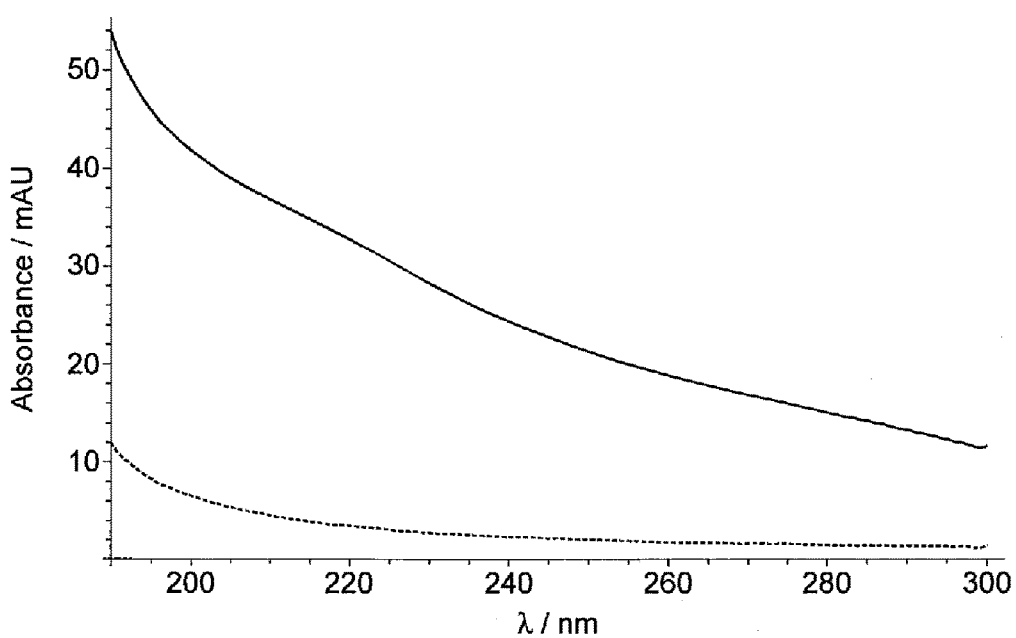
FIGS. 4 to 6 show example baseline reference spectra corresponding to the example scale inhibiting polymer reference spectrum of FIG. 3.
Figure 5:
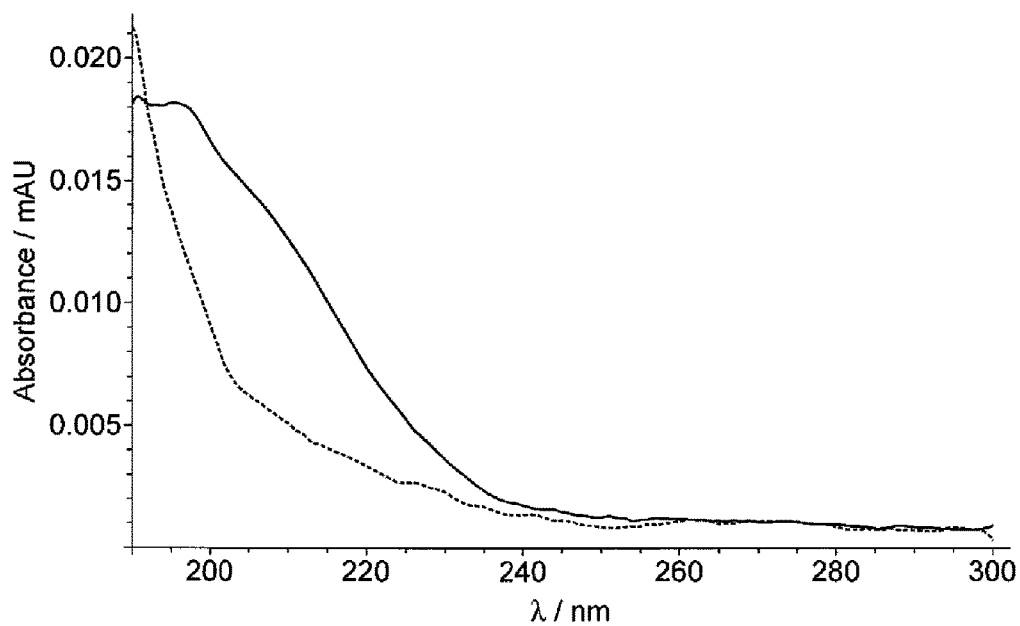
Figure 6:
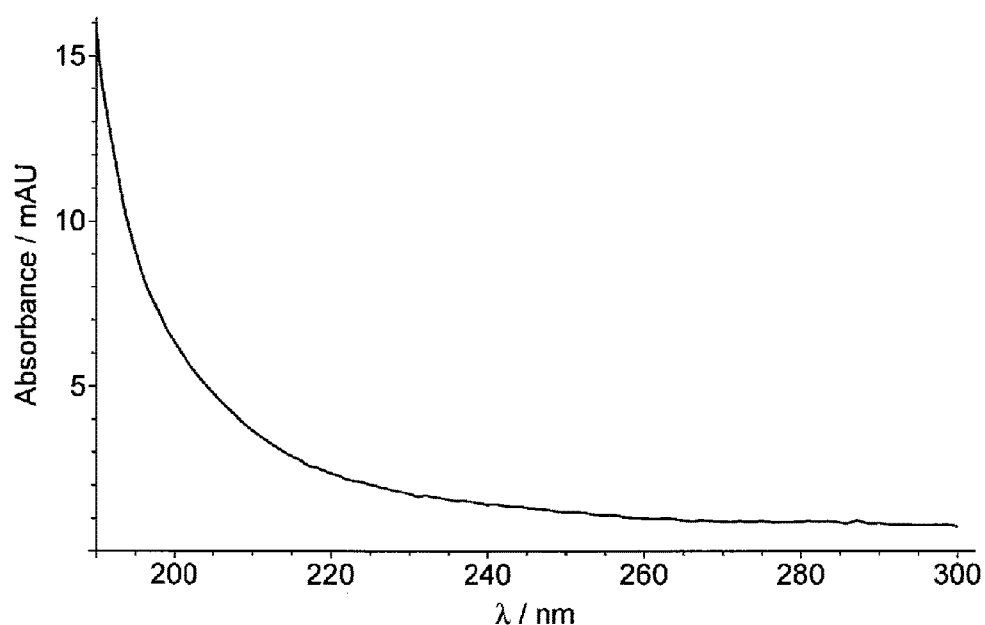

FIGS. 4 to 6 show some example baseline reference spectra corresponding to the example tagged inhibitor reference spectrum of FIG. 3. In this case there are two untagged inhibitor spectra (FIG. 4), two HPLC water static UV spectra (FIG. 5), and one produced water spectrum (FIG. 6). The relative magnitudes of the reference spectra are unimportant at this stage, because they are all freely variable in the curve-fitting process performed by the algorithm. Data representing the baseline reference spectra, together with any tagged inhibitor concentration calibration factors corresponding to the GPC column(s) being used, are input into the system 6 at step S104.

The reference spectrum of the untagged inhibitor is necessary to account for interactions between the tagged inhibitors and the GPC column, which in turn cause the measured PDA spectra to differ from the spectrum of the tagged inhibitor as observed under static UV experiments.

Referring to FIG. 4, a single GPC experiment can be performed on the untagged inhibitor. This produces a series of spectra over the elution time. An algorithm similar to that of FIG. 2 can be applied to the resulting spectra in order to determine the reference spectrum or spectra of the untagged inhibitor. The algorithm fits each individual GPC spectrum from the inhibitor elution individually to all other spectra in the elution to find the two spectra which, in linear combination, fit across the whole elution with the smallest root mean square error.

Referring to FIG. 5, two further reference spectra are derived from static UV experiments on two samples of water, e.g. HPLC (i.e. pure or de-ionised) water, that have been exposed to laboratory air. Two samples of water are provided. One sample is degassed using nitrogen to remove dissolved oxygen. The static UV spectrum of each sample is then measured. Laboratory air (i.e. a sample of the air present in the laboratory) is then introduced, for example by pipette, into each sample. The static UV spectrum of each sample is measured again. Further laboratory air is introduced into each sample and the static UV spectrum of each sample is measured once again. This process is repeated until the spectrum for each sample closely matches the preceding spectrum. For each sample, a reference spectrum is obtained by taking the last measured spectrum and fitting each of the other spectrums for that sample to that last spectrum. An average of all of these fits is determined, and that becomes the reference spectrum for that sample of water.

Obtaining reference spectra for samples of water containing contaminants present in the laboratory has been found to be useful. It has been found that contaminants present in the laboratory absorb at low wavelengths. This absorption can "hide" absorptions at low wavelengths of the tagged scale inhibitor. By taking account of the absorptions from the contaminants, the absorption of the tagged scale inhibitors at low wavelengths can be discerned.

The produced water reference spectrum of FIG. 6 is preferably taken from a sample of produced water from the relevant commingled flow. This reference spectrum can be a GPC spectrum of the produced water with a significant total absorption between the selected wavelength range, e.g. 190 to 300 nm. This spectrum can be identified by plotting the total absorption for each spectrum as a function of elution time (this is the chromatogram). The highest peak on the chromatogram corresponds to the greatest absorption. Accordingly, taking the GPC spectrum which corresponds to this absorption peak can give a suitable reference spectrum for produced water. Alternatively, this reference spectrum can be derived by an algorithm similar to that described for the untagged inhibitor reference spectra described above.

It is envisioned that, in certain situations, it may not be possible to obtain a sample of produced water free from the scale inhibitor. This would occur where the scale inhibitor has already been used in one or more wells producing fluid into the commingled flow. In such a situation, it would not be possible to obtain an accurate reference spectrum or spectra to represent background absorptions present in the produced water, since the scale inhibitor already present would also have an absorption in the GPC process described here. In such situations, one or more reference spectrum/spectra can be used to represent produced fluid produced from the one or more rock formations.

Chemical species known to be present in the produced water, such as production chemicals other than the scale inhibitor, are recorded. One or more reference spectrum/spectra are determined for those chemicals which have an absorption in the selected wavelength range, e.g. 190 nm to 300 nm. For each chemical having an absorption in the selected wavelength range, at least one reference spectrum is determined using the same method as described above in connection with the untagged scale inhibitor reference spectra. These reference spectra become part of the baseline reference spectra and can be used in the algorithm of FIG. 2 instead of using a reference spectrum derived from actual produced water.

The static UV reference spectra of the tagged inhibitors themselves can be refined by a GPC-based algorithm. This algorithm takes as input a GPC experiment on a single tagged inhibitor in water, such as HPLC water. It assumes that if the baseline of a GPC spectrum is well-modelled, then after subtraction of a modelled baseline spectrum that is determined as described with respect to FIG. 2 below, the remaining absorption must be due to the tagged inhibitor. This remaining absorption is therefore output as the tagged inhibitor's reference spectrum. Following the method described with respect to FIG. 2, a GPC experiment of the tagged inhibitor of interest is performed. This results in a series of UV spectra over the elution time. For each measured spectrum, the reference spectra (typically the static UV spectrum of the tagged inhibitor of interest, the untagged scale inhibitor reference spectra, the reference spectra of water exposed to laboratory air and the produced water reference spectrum) are combined and the corresponding multiplicative factors recorded, as described below in connection with steps S108 and S109. The reference spectra for the untagged scale inhibitor, water exposed to laboratory air and the produced water are each multiplied by their corresponding multiplicative factors and then linearly combined to produce a "baseline" reference spectrum, as described below in connection with FIG. 8. This baseline reference spectrum is subtracted from the measured spectrum in question to produce a first refined reference spectrum for the tagged scale inhibitor.

This process is repeated for each measured spectrum over the elution time, resulting in a series of refined reference spectra for the tagged scale inhibitor. The spectrum which has the greatest absorption can be chosen as the final refined reference spectrum for the tagged scale inhibitor. To identify the spectrum with the greatest absorption, the total absorption for each spectrum over the whole elution time can be plotted against time (resulting in a chromatogram). The peak of the chromatogram corresponds to the greatest absorption and so the spectrum which corresponds to that peak can be used as the reference spectrum for the tagged scale inhibitor.

Refining the reference spectrum for the tagged inhibitor in this way can be appropriate where more than one tagged inhibitor is present in the sample of commingled fluid to be tested.

The computer-implemented method of the present invention is based on replacing static UV spectra for the tagged inhibitors with more accurate spectra derived from high-concentration GPC experiments.

In addition, the derivation of the other reference spectra is a process that can be automated if the appropriate experiments are performed; this allows the algorithm to adapt to new conditions such as different GPC columns or column conditions, or changes in the composition of processed water.

As can be seen from step S105, a number of GPC columns can be used in multiple laboratory experiments with samples of the same fluid. Each GPC column (A, B, C . . . ) has different chemical properties and hence its own unique reference spectra and elution time profile, together with its own set of calibration factors (one each per tagged inhibitor).

At step S106, variable i (representing a sequence of time steps over the GPC elution time) is defined by the algorithm as 0, the total number of measured GPC spectra is defined as n, and the total number of reference spectra is defined as m. At step S107, the measured GPC spectrum is isolated at time t(i), where the time t is measured in discrete integer steps of i between 0 and n. In the example described t(i+1)=t(i)+0.1 seconds.

Figure 7:
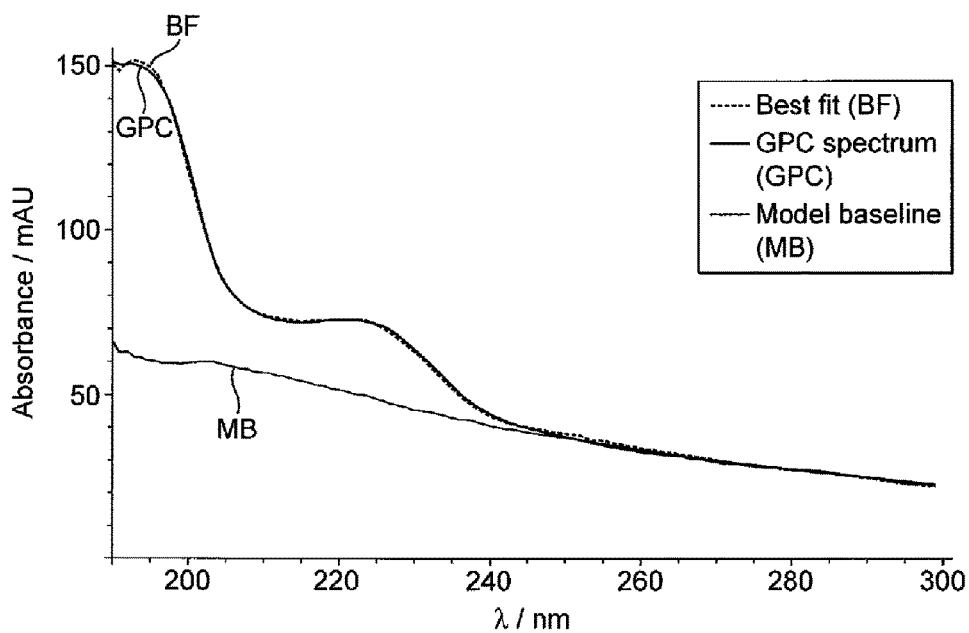
FIG. 7 shows a measured absorption spectrum together with models of the reference spectra and baseline reference spectra, as modelled by the computer program of the present invention.

At step S108, for each measured GPC-UV spectrum, the algorithm finds a best-fit linear combination of all of the reference spectra, plus a constant offset (kc), to produce a modelled spectrum. An example GPC-UV spectrum and corresponding modelled spectrum are shown in FIG. 7. The curve labelled MB in FIG. 7 is the modelled baseline, which is the part of the model spectrum composed of baseline reference spectra. The best-fit (labelled BF) is a linear combination of the m reference spectra $T_1, T_2, \ldots, T_m$ of the form $k_1*T_1+k_2*T_2+ \ldots +k_m*T_m+kc$, where $k_1, k_2, \ldots, k_m$ are multiplicative constants or factors. The multiplicative factors are unconstrained variables whose values are optimised by the fitting subroutine of the algorithm. The fitting subroutine uses, for example, the Levenberg-Marquadt algorithm, such that the total root-mean-square difference between the quantity $k_1*T_1+k_2*T_2+ \ldots +k_m*T_m+kc$ and the measured GPC spectrum is minimised. In step S109, the multiplicative factors are recorded by the system 6 for each reference spectrum for the time step i being considered.

Table 1 below shows the best-fit multiplicative factors multiplied by each reference spectrum to obtain the best-fit in FIG. 7.

TABLE 1

| Reference spectrum, $T_i$ | Best-fit scaling factor, $k_i$ |
| --- | --- |
| Tagged inhibitor | 0.3427 |
| Untagged inhibitor 1 | 1.682 |
| Untagged inhibitor 2 | −3.658 |
| HPLC water static UV 1 | 278.3 |
| HPLC water static UV 2 | −1816 |
| Produced water | 2.999 |
| Constant offset | 6.029 |

This fitting process is repeated for each GPC-UV spectrum, and the scaling factor $k_i$ for each tagged inhibitor is recorded for each spectrum. In the example above there is only one tagged inhibitor and its factor is 0.3427.

Figure 8:
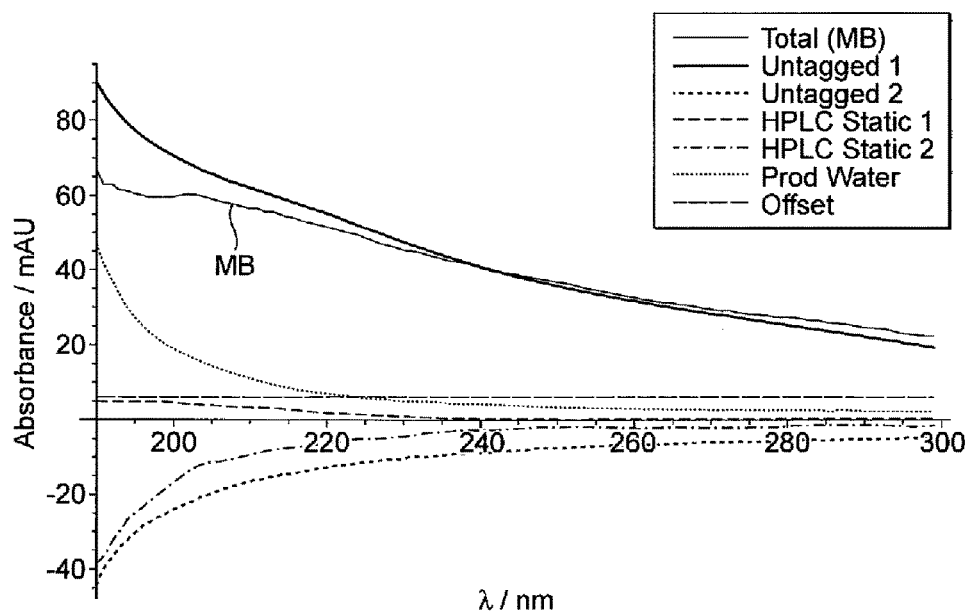
FIG. 8 shows the reference spectra used by the computer program to generate the modelled baseline spectrum of FIG. 7.

FIG. 8 shows the modelled baseline in more detail, with each of the scaled baseline reference spectra. The curve labelled MB—which is the same as that of FIG. 7—is the sum of all of the other curves of FIG. 8.

Figure 9:
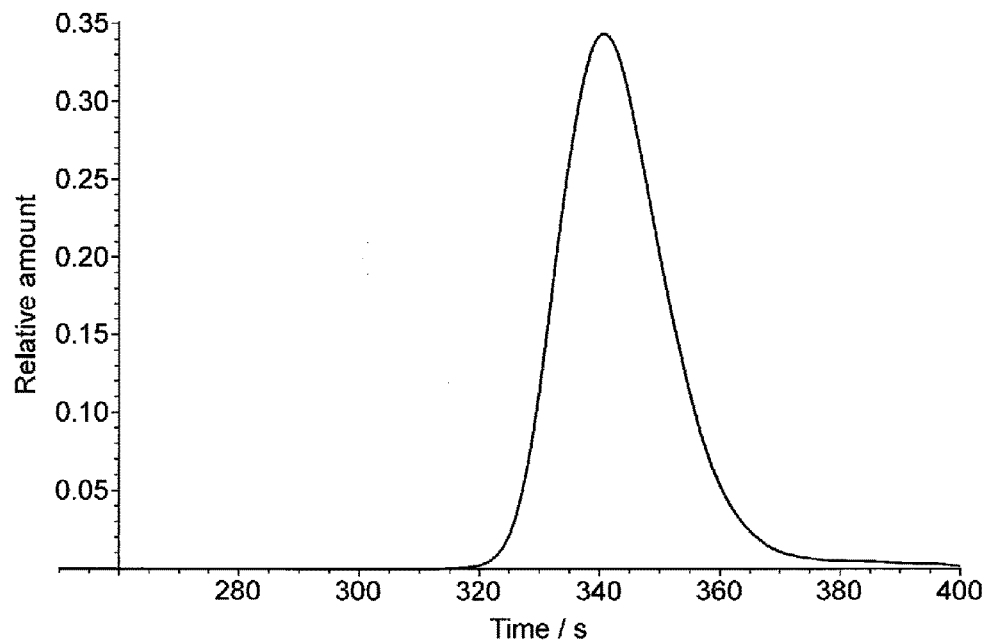
FIG. 9 shows a graph of relative scale inhibiting polymer concentration against time as determined by the computer program of the present invention.

From step S110 of FIG. 2 onwards, each tagged inhibitor T is considered individually in order to determine its respective concentration. FIG. 9 shows a measure of the multiplicative factor of a tagged inhibitor, which is equivalent to the relative retrieved concentration of the tagged inhibitor, across the whole of the respective tagged inhibitor's elution time in seconds. Referring to step S121 of FIG. 2, the sum of all the discrete y-axis points (i.e. the sum of the factors at each time step i) over the elution time provides an indication of concentration that is proportional to the absolute concentration of the tagged inhibitor. However, summing over the whole of the elution time can sometimes lead to erroneous results. Therefore, a start point $i_1$ and end point $i_2$ can be found and the summation can be limited between these two points to improve the accuracy of the concentration value determined.

There are a number of ways in which $i_1$ and $i_2$ can be found. For example, the values can be determined by: manual selection by a system operator; determining the time steps i over which the multiplicative factor of the retrieved tagged inhibitor concentration is greater than a predefined threshold value, with $i_1$ being the first and $i_2$ being the last of these points; determining the time steps i over which an error in the best-fit is lower than a predefined threshold value, with $i_1$ being the first and $i_2$ being the last of these points; or determining the time steps i over which a least squares correlation coefficient of a linear model generated for each tagged inhibitor is greater than a predefined threshold value, with $i_1$ being the first and $i_2$ being the last of these points.

Figure 10:
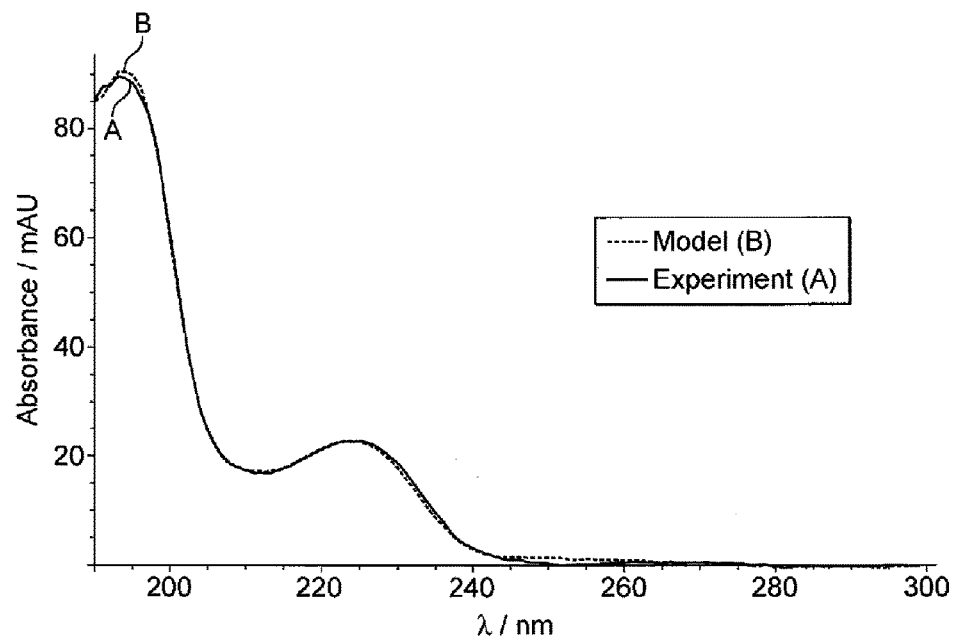
FIG. 10 shows the measured and modelled absorption spectra of FIG. 7, with the modelled baseline spectra of FIG. 8 subtracted therefrom.

Referring again to FIG. 2, the modelled baseline can be used in a process described with respect to steps S110 to S120 to determine appropriate values of $i_1$ and $i_2$. The algorithm selects a first tagged inhibitor T (step S110), and proceeds to calculate the quality of fit and the error associated with the fit. In step S111 the modelled baseline (including all tagged inhibitors other than n is subtracted from the measured absorption spectrum, and this result is defined as A. In step S112 the modelled baseline is subtracted from the modelled spectrum, and this result is defined as B. FIG. 10 shows the results of these subtractions. In the case of the modelled spectrum, it should be appreciated that subtracting the modelled baseline leaves only the tagged inhibitor T reference spectrum multiplied by its best-fit factor, i.e. $B=k_1*T_1$ for tagged inhibitor $T_1$.

Both of the curves in FIG. 10—A for the experimental curve and B for the modelled curve—consist of points measured at the same wavelengths. In step S113, the algorithm tabulates each point of A against the corresponding point of B at the same wavelength. For each wavelength, the absorbance from A is plotted against the absorbance from B and a best-fit linear model is applied in step S114. If the model is a perfect fit, this plot would be a 1:1 straight line; in reality, there will always be some deviation.

Figure 11:
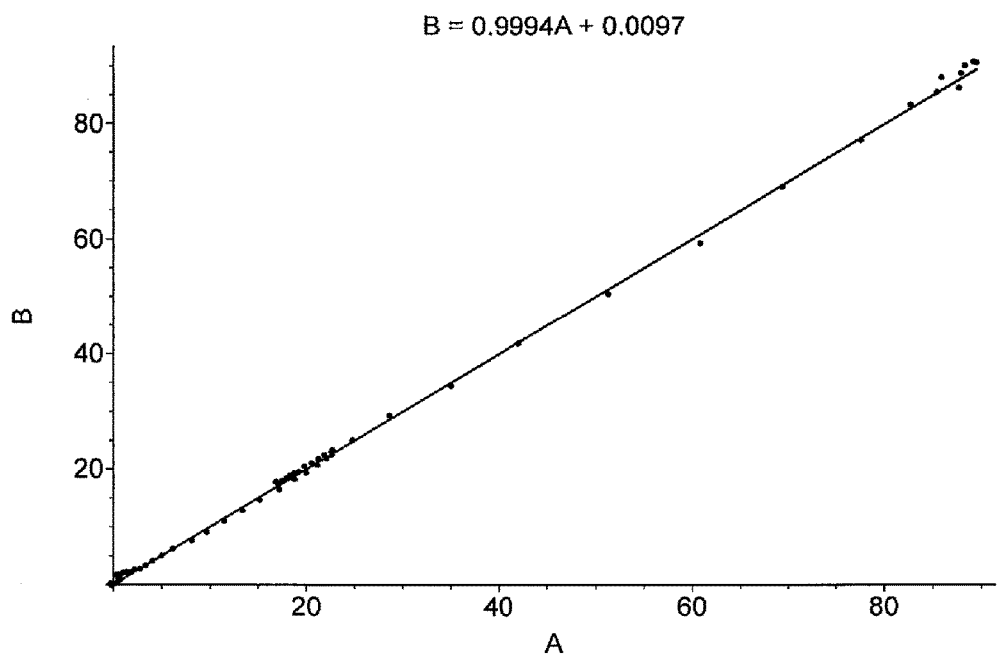
FIG. 11 shows a linear best-fit of the spectra of FIG. 10 plotted against one another at equivalent wavelengths.

FIG. 11 shows a plot of A vs. B for this example. The least-squares regression line for this data is close to a 1:1 A=B line, because the model is a very good fit to the observed spectrum in this example. The standard error in the gradient of this line can be calculated (step S115). In this case, the result is $2.403*10^{-3}$. This is a measure of the error in the fit for this spectrum.

In a similar way, the quality of fit can be measured by recording the least-squares regression coefficient $R^2$. In the example of FIG. 11, $R^2=0.9994$.

In experiments where more than one tagged inhibitor is present, the process of steps S111-S115 is performed independently for each tagged inhibitor; in step S116, the algorithm asks whether the error has been recorded for every tagged inhibitor present, and if not (step S116=False) then the next tagged inhibitor is selected at step S117 and the process returns to step S111. For example, in a mixture of tagged inhibitors $T_1$ and $T_2$, the quality of fit for tagged inhibitor $T_1$ is calculated by considering the reference spectrum for $T_2$ as part of the modelled baseline, subtracting it along with all the baseline reference spectra, and proceeding to construct the A vs. B plot. Similarly, for tagged inhibitor $T_2$, the $T_1$ reference spectrum is considered as part of the model baseline.

Once the multiplicative factors, errors and $R^2$ values have been calculated for each tagged inhibitor over every spectrum in the GPC experiment (S116=True), they can each be plotted as a function of time. At step S118, the algorithm asks whether i=n, i.e. whether all time steps over the tagged inhibitor's elution time have been considered, and if not (step S118=False) then the algorithm selects the next time step such (step S119) such that i=i+1 and returns to step S107 to repeat the process for that time step. As explained above, FIG. 9 shows the multiplicative factor of the tagged inhibitor, which is equivalently the relative retrieved concentration of the tagged inhibitor present, across the whole of the tagged inhibitor's elution.

Figure 12:
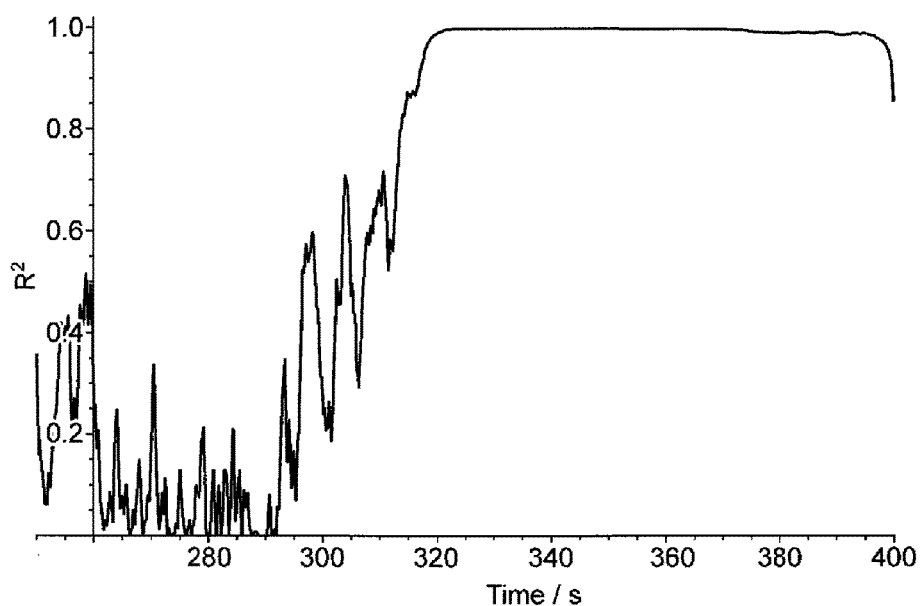
FIG. 12 shows a plot of the least squares linear coefficient for the modelled spectrum as a function of time.

If, at step S118, i=n, then $i_1$ and $i_2$ are found based on the calculated error data. One possible condition to find the start and end points $i_1$ and $i_2$ is to find the first and last times at which the $R^2$ value is greater than a certain threshold. A plot of $R^2$ as a function of time for the example of FIG. 9 is shown in FIG. 12. If the threshold is defined as $R^2=0.95$, the limits are $i_1=317.9$ s and $i_2=399.2$ s.

Referring again to FIG. 2, at step S121 the multiplicative factors for each tagged inhibitor are summed over all i from $i_1$ to $i_2$; for tagged inhibitor $T_1$ this is the sum of $k_1(i)$ over all $i_1$ to $i_2$. In the example of FIG. 9, applying the time points of $i_1=317.9$ s and $i_2=399.2$ s as summation limits and performing the sum gives a result of 73.83 (whose units are arbitrary at this stage).

As an alternative to calculating $i_1$ and $i_2$ and summing the multiplicative factors between these two times, the relative concentration of a tagged inhibitor can be derived by comparing the measured multiplicative factor curve for that tagged inhibitor, derived using the process described above in connection with FIG. 9, with a reference multiplicative factor curve for that tagged inhibitor. The reference multiplicative factor curve is derived by carrying out a GPC experiment for the tagged scale inhibitor in water, as described elsewhere in this application. The tagged scale inhibitor is dissolved in water at a concentration high enough so that noise from the PDA detector has negligible effect. For each spectrum over the elution time, the reference spectra for the tagged scale inhibitor, the untagged scale inhibitor, the produced water and the water exposed to laboratory contaminants are linearly combined according to the process described above with respect to steps S108 and S109, and the multiplicative factors for the reference spectra are recorded. The multiplicative factors for the tagged scaled inhibitor are plotted as a function of time to produce the reference multiplicative factor curve.

By plotting the multiplicative factors for the measured multiplicative factor curve against the multiplicative factors for the reference multiplicative factor curve, an indication of the total concentration of the tagged scale inhibitor can be obtained. The gradient of the plot of "measured" against "reference" multiplicative factor curves reflects the relative concentration of the tagged inhibitor. The error in the calculated gradient gives an indication of the error in the process: the greater the error in the gradient, the greater the error in the calculated relative concentration.

As an additional quality control check, if the relative concentration determined using this method does not closely match the relative concentration determined using the method described above based on identifying start and end times $i_1$ and $i_2$, this is indicative of an anomaly.

At step S122, the result (i.e. the relative concentration) is multiplied by the respective tagged inhibitor's calibration factor. As described above, by calibrating relative to a set of one or more known concentration standards prepared in similar conditions, the absolute concentration of the inhibitor can be derived. In the example of FIGS. 3-12, applying the calibration factor of 1.37 gives an output (step S123) concentration of 101.1 ppm for the tagged inhibitor under consideration.

Some of the methods described above for determining the reference spectra (for example the untagged inhibitor and produced water reference spectra) involve taking a series of measured spectra from a GPC experiment and fitting each individual GPC spectrum to all the other spectra in the series to find the spectra which, in linear combination, fit across the whole elution with the smallest root mean square error. When deriving the reference spectra for the untagged scale inhibitor, it is typically found that two reference spectra can be identified which can be linearly combined to fit across the rest of the spectra from the GPC experiment. When deriving the reference spectra for the produced water, three reference spectra may be used to fit across the other spectra. The number of reference spectra can depend on how widely the spectra vary over the whole elution time. If there is a large variation over the elution time, more spectra (such as three) may be needed to enable a good fit across the whole elution time; if there is little variation over the elution time, fewer reference spectra (such as two) may suffice.

Figure 13:
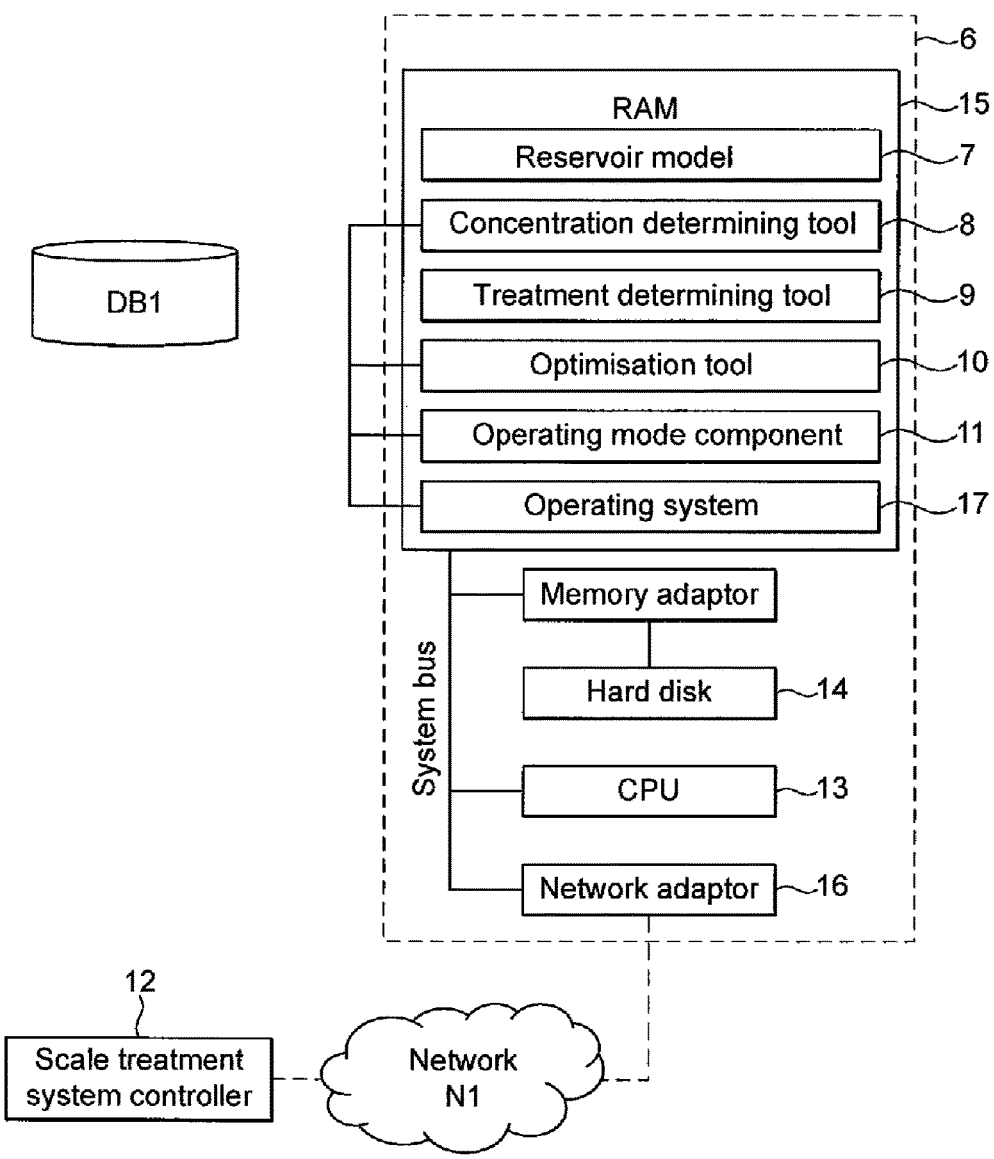
FIG. 13 shows a system according to the present invention.

In order to determine the concentrations of the various commingled tagged inhibitors, the system 6 comprises suitable computer-implemented models, software tools and hardware, as shown in FIG. 13. A reservoir model 7 may be employed by the system 6. As known in the art, a reservoir model is a conceptual 3-dimensional construction of a reservoir that is constructed from incomplete data with much of the inter-well space estimated from data obtained from nearby wells or from seismic data.

Software tools (computer programs) in the form of a concentration determining tool 8 and a treatment determining tool 9, are also employed by the system 6. The concentration determining tool can calculate the individual tagged inhibitor concentrations using an algorithm as explained above. Using the reservoir model 7, the treatment determining tool 9 can use information such as the volume and shape of the relevant reservoir(s), the porosity of the oil-bearing rock formations, the location of existing production wells and injection wells, in combination with the results of the concentration determining tool 8, to provide an indication as to the possible volumes, concentrations and placement of tagged scale inhibitors required in future waterfloods or squeeze treatments.

An optimisation tool 10 may be provided to assist in the planning of treatments. The optimisation tool 10 may be used in conjunction with the treatment determining tool 9 to compute an optimal future treatment plan, based on input data including the determined concentrations and required treatments for particular reservoirs or wellbores. In the case where a number of treatments are possible, the optimisation tool 10 may be programmed with rules that take into account additional data representing, for example, threshold values representing practical limits to the implementation of treatments, for example, timing or other practical constraints. In this way, the optimisation tool 10 can determine an optimum treatment plan to ensure that the scale inhibitor levels are automatically maintained at an optimum concentration as far as possible.

The system 6 further comprises an operating mode component for determining an operating mode as explained further below with reference to FIG. 14. The system 6 is preferably operatively connected to a controller 12 of a scale treatment system (not shown), for example via the network N1. The controller 12 of the treatment system is automatically configured with one or more operating modes determined by the system 6, the controller 12 being arranged to apply the one or more operating modes.

In one arrangement, referring to FIG. 13, the concentration determining tool 8 and optionally the reservoir model 7, the treatment determining tool 9, the optimisation tool 10 and the operating mode component 11 are executed by the system 6. The system 6 can comprise conventional operating system and storage components such as a system bus connecting a central processing unit (CPU) 13, a hard disk 14, a random access memory (RAM) 15, and I/O and network adaptors 16 facilitating connection to user input/output devices (e.g. for receiving input data) and interconnection with other devices on a network N1. The RAM 15 contains operating system software 17 which controls, in a known manner, low-level operation of the system 6. The server RAM 13 contains the software tools and models 7, 8, 9, 10 and 11 during execution thereof. Each item of software is configurable with measurement and/or predetermined data stored in one or more databases or other storage components which are operatively coupled or connected to the system 6; in the system of FIG. 13, storage component DB1 stores all such data relating to the various software tools and models, and is accessible thereby.

Input data received by receiving means of the system 6 comprise the measured absorption spectra, a tagged inhibitor reference spectrum per tagged inhibitor present, baseline reference spectra and calibration factors per GPC column, data relating to the injection volume and GPC column identity and any other data required by the system software, such as a definition of the time step value i.

The concentration determining tool may comprise a bespoke software program.

Figure 14:
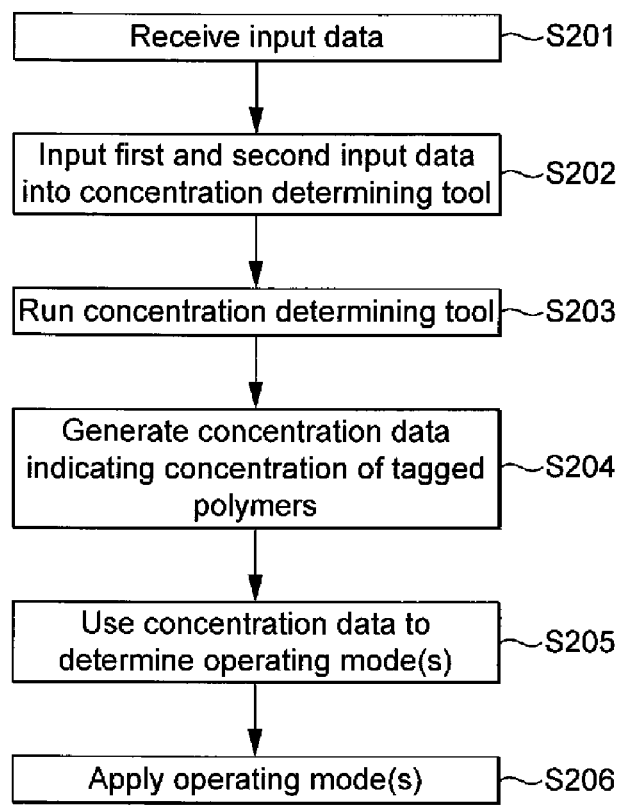
FIG. 14 shows the steps taken in determining an operating mode of a scale treatment system according to the present invention.

Referring to FIG. 14, the steps involved in a first embodiment of a computer-implemented method for determining one or more operating modes for the scale treatment system are shown.

In step S201, the input data is received by the scale treatment system 6.

At step S202, the input data are input into the concentration determining tool 8, the calculations of which are described above in relation to FIGS. 2 to 12. The concentration determining tool 8 is then run in step S203, and generates, at step S204, concentration data indicative of the individual concentrations of the tagged scale inhibiting polymers present in the fluid sample 1. This data may be output in various forms.

At step S205, the generated concentration data are used to determine one or more operating modes of the scale treatment system. The operating mode can represent an instruction or suggested setting for the scale treatment system, which can subsequently be applied to the scale treatment system.

Software executed by the CPU 13 of the system 6 determines, on the basis of the determined concentrations, the one or more operating modes of the scale treatment system. The reservoir model 7, the treatment determining tool 9 and/or the optimisation tool 10 may be configured in conjunction with or as part of the operating mode component 11 to determine the operating mode(s) upon generation of the concentration data. Additional technical and physical constraints determined by the system software may be taken into account in order to determine the operating mode, and can be stored and accessed from the database(s) DB1 as necessary.

For example, the operating mode can comprise an instruction to go ahead with a treatment of a particular wellbore determined by the treatment determining tool 9 or not, based on a queue of required treatments generated by the optimisation tool 10. Alternatively or additionally, the operating mode can comprise one or more specific configuration settings for the scale treatment system, such as an injection time, volume, pressure, etc.

The operating mode component 11 is configured to use a predetermined set of rules in conjunction with input data such as the calculated concentration(s), in order to determine the operating mode. These rules are stored in and accessible from the database(s) DB1 as necessary.

The computer-implemented method can further include an optional step, S206, of applying or inputting the determined operating mode into the controller 12 of the scale treatment system.

The above embodiments are to be understood as illustrative examples of the invention. Further embodiments of the invention are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A non-transitory computer-readable medium encoded with executable code comprising instructions to determine the concentration of one or more scale inhibiting polymers, each scale inhibiting polymer comprising a different chemical marker, in a fluid received from one or more porous and permeable hydrocarbon-bearing rock formations, the fluid comprising a plurality of commingled said scale inhibiting polymers, wherein the executable code, when executed by a processor, causes the processor to:
   receive first input data representing a measured absorption spectrum, within a predetermined wavelength range, of the commingled scale inhibiting polymers, wherein the measured absorption spectrum is measured using a detector after chromatographic separation of the fluid;
   receive second input data representing reference absorption spectra, the reference absorption spectra comprising:
   a) an absorption spectrum, over the predetermined wavelength range, of each of the scale inhibiting polymers; and
   b) baseline reference absorption spectra of other chemicals having absorbance values within the predetermined wavelength range that are expected to be present in the fluid;
   at each of a plurality of discrete time steps over an elution time for the separation, determine a factor for each reference absorption spectrum that results in a modelled spectrum comprising a best-fit linear combination of the second input data to the first input data; and
   for each scale inhibiting polymer:
   use the factors corresponding to the absorption spectrum of said scale inhibiting polymer that have been determined for a predetermined number of said discrete time steps to determine an indication of the concentration of the scale inhibiting polymer.

2. The non-transitory computer-readable medium of claim 1, wherein the baseline reference absorption spectra comprise at least:
   i) an absorption spectrum of each scale inhibiting polymer in the absence of its chemical marker;
   ii) an absorption spectrum of produced fluid or of fluid representing produced fluid produced from the one or more rock formations; and
   iii) an absorption spectrum of water comprising other chemicals having absorbance values within the predetermined wavelength range that are expected to be present in the fluid.

3. The non-transitory computer-readable medium of claim 2, wherein the absorption spectrum of water comprising other chemicals having absorbance values within the predetermined wavelength range comprises at least one absorption spectrum of water which has been exposed to air from an atmosphere.

4. The non-transitory computer-readable medium of claim 2, wherein the absorption spectrum of water comprising other chemicals having absorbance values within the predetermined wavelength range comprises at least two absorption spectra of water which has been exposed to air from an atmosphere, at least one of which is an absorption spectra of water which has been degassed before being exposed to said atmospheric air.

5. The non-transitory computer-readable medium of claim 2, wherein execution of the executable code causes the processor to derive the absorption spectrum of each scale inhibiting polymer in the absence of its chemical marker and the absorption spectrum of produced fluid or of fluid representing produced fluid produced from the one or more rock formations by causing the processor to select at least one spectrum from absorption spectra measured using a detector after chromatographic separation of said scale inhibiting polymer in the absence of its chemical marker and of said fluid.

6. The non-transitory computer-readable medium of claim 1, wherein the absorption spectrum, over the predetermined wavelength range, of each of the scale inhibiting polymers is derived through a measurement of the static absorption spectrum of each individual scale inhibiting polymer dissolved in water.

7. The non-transitory computer-readable medium of claim 6, wherein the executable code further causes the processor to refine the absorption spectrum of each individual scale inhibiting polymer by causing the processor to:
   i) receive third input data representing measured spectra, within a predetermined wavelength range, of the scale inhibiting polymer in water, wherein the measured spectra are measured using a detector after chromatographic separation of the scale inhibiting polymer in water;
   ii) for each measured spectrum in the third input data, determine a factor for each of the reference absorption spectra that results in a modelled spectrum comprising a best-fit linear combination of the reference absorption spectra to said measured spectrum and subtract the baseline reference absorption spectra multiplied by their corresponding factors, from said measured spectrum to produce refined reference absorbance data; and
   iii) select from the refined reference absorbance data produced from all of the measured spectra, the refined reference absorbance data which corresponds to the greatest absorption.

8. The non-transitory computer-readable medium of claim 1, wherein the executable code further causes the processor to, for each scale inhibiting polymer, sum the factors corresponding to the absorption spectrum of said scale inhibiting polymer that have been determined for a predetermined number of said discrete time steps, and to determine the predetermined number of discrete time steps over which the factors are summed, by:
   determining the time steps over which the factor of the scale inhibiting polymer is greater than a predefined threshold value; or
   determining the time steps over which an error in the best-fit is lower than a predefined threshold value; or
   determining the time steps over which a least squares correlation coefficient of a linear model generated for each scale inhibiting polymer is greater than a predefined threshold value.

9. The non-transitory computer-readable medium of claim 1, wherein the executable code further causes the processor to:
   for a particular scale inhibiting polymer under consideration, and at each of a plurality of discrete time steps across the measured absorption spectrum, produce a modelled baseline spectrum based on a best-fit of a linear combination of the baseline reference absorption spectra and each of the scale inhibiting polymer reference spectra other than that of a specific said scale inhibiting polymer being considered, to the measured absorption spectrum;

determine, from the modelled baseline spectrum, a corresponding factor that is applied, in order to produce the best-fit, to each baseline absorption spectrum and each of the scale inhibiting polymer reference spectra other than a specific said scale inhibiting polymer being considered at each of said discrete time steps;

subtract the modelled baseline spectrum from the measured absorption spectrum to define a first set of absorbance data;

subtract the modelled baseline spectrum from the relevant modelled spectrum to define a second set of absorbance data;

apply a best-fit linear model to a plot of the first set of absorbance data against the second set of absorbance data; and calculate at least one of:
a standard error in the gradient of the linear model; and
a least squares correlation coefficient of the linear model.

10. The non-transitory computer-readable medium of claim 1, wherein the executable code further causes the processor to determine an indication of the concentration of the each scale inhibiting polymer by comparing the factors corresponding to the absorption spectra of said scale inhibiting polymer that have been determined for a predetermined number of said discrete time steps against reference factors corresponding to reference absorption spectra of said scale inhibiting polymer.

11. The non-transitory computer-readable medium of claim 10, wherein the executable code further causes the processor to:

receive reference input data representing measured spectra, within a predetermined wavelength range, of the scale inhibiting polymer in water, wherein the measured spectra are measured using a detector after chromatographic separation of the scale inhibiting polymer in water;

for each measured spectrum in the reference input data, determine a reference factor for each of the reference absorption spectra that results in a modelled spectrum comprising a best-fit linear combination of the reference absorption spectra to said measured spectrum; and determine a gradient of a plot of the factors corresponding to the absorption spectra of said scale inhibiting polymer that have been determined for a predetermined number of said discrete time steps, against reference factors corresponding to reference absorption spectra of said scale inhibiting polymer.

12. The non-transitory computer-readable medium of claim 1, wherein the executable code further causes the processor to calibrate the summed factors according to a calibration factor to determine an absolute concentration of the scale inhibiting polymer, the calibration factor for each scale inhibiting polymer being calculated by the executable code causing the processor to:

receive the second input data representing the reference absorption spectra;

receive third input data representing a measured absorption spectrum, within a predetermined wavelength range, of the respective scale inhibiting polymer;

at each of a plurality of discrete time steps over an elution time of the respective scale inhibiting polymer, determine a factor for each reference absorption spectrum that results in a modelled spectrum comprising a best-fit linear combination of the second input data to the third input data;

sum the factors corresponding to the measured absorption spectrum of said scale inhibiting polymer that have been determined for a predetermined number of said discrete time steps to determine an output concentration; and divide the known concentration by the output concentration to calculate the respective calibration factor.

13. A system arranged to determine the concentration of one or more scale inhibiting polymers, each scale inhibiting polymer comprising a different chemical marker, in a fluid received from one or more porous and permeable hydrocarbon-bearing rock formations, the fluid comprising a plurality of commingled said scale inhibiting polymers, the system comprising:

data receiving means arranged to receive:
first input data representing a measured absorption spectrum, within a predetermined wavelength range, of the commingled scale inhibiting polymers, wherein the measured absorption spectrum is measured using a detector after chromatographic separation of the fluid; and second input data representing reference absorption spectra, the reference absorption spectra comprising:
c) an absorption spectrum, over the predetermined wavelength range, of each of the scale inhibiting polymers; and
d) baseline reference absorption spectra of other chemicals having absorbance values within the predetermined wavelength range that are expected to be present in the fluid;

concentration determining means configured to:
at each of a plurality of discrete time steps over an elution time for the separation, determine a factor for each reference absorption spectrum that results in a modelled spectrum comprising a best-fit linear combination of the second input data to the first input data; and for each scale inhibiting polymer:
use the factors corresponding to the absorption spectrum of said scale inhibiting polymer that have been determined for a predetermined number of said discrete time steps to determine an indication of the concentration of the scale inhibiting polymer.

14. The system of claim 13, further comprising first absorption spectrum deriving means configured to derive the absorption spectrum of each scale inhibiting polymer in the absence of its chemical marker by selecting at least one spectrum from absorption spectra measured using a detector after chromatographic separation of the scale inhibiting polymer in the absence of its chemical marker.

15. The system of claim 13, further comprising second absorption spectrum deriving means configured to derive at least one absorption spectrum of produced fluid or of fluid representing produced fluid produced from the one or more rock formations by selecting at least one spectrum from absorption spectra measured using a detector after chromatographic separation of said fluid.

16. The system of claim 13, further comprising third absorption spectrum deriving means configured to derive at least one absorption spectrum of water comprising other chemicals having absorbance values within the predetermined wavelength range by selecting at least one spectrum from absorption spectra of water which has been exposed to air from the atmosphere in which the spectra have been measured.

17. The system of claim 13, wherein the data receiving means is further arranged to receive third input data representing measured spectra, within a predetermined wavelength range, of the scale inhibiting polymer in water, wherein the measured spectra are measured using a detector after chromatographic separation of the scale inhibiting polymer in water; the system further comprising refining means configured to, for each scale inhibiting polymer, refine an absorption spectrum of said scale inhibiting polymer by:
  i) for each measured spectrum in the third input data, determining a factor for each of the reference absorption spectra that results in a modelled spectrum comprising a best-fit linear combination of the reference absorption spectra to said measured spectrum and subtracting the baseline reference absorption spectra multiplied by their corresponding factors, from said measured spectrum to produce refined reference absorbance data; and
  ii) selecting from the refined reference absorbance data produced from all of the measured spectra, the refined reference absorbance data which corresponds to the greatest absorption.

18. The system of claim 13, wherein the system further comprises operating mode determining means arranged to determine, on the basis of the determined concentration of the respective one or more scale inhibiting polymers comprising said chemical markers, an operating mode of a scale inhibitor treatment system.

19. The system of claim 18, wherein the system is operatively connected to a controller of the scale inhibitor treatment system such that the controller of the scale inhibitor treatment system is automatically configured with the one or more operating modes determined, the controller being arranged to apply the one or more operating modes.

* * * * *